US009604044B2

United States Patent
Eckstein et al.

(10) Patent No.: US 9,604,044 B2
(45) Date of Patent: Mar. 28, 2017

(54) CONNECTION DEVICE FOR USE IN THE NEGATIVE PRESSURE TREATMENT OF WOUNDS

(71) Applicant: Paul Hartmann AG, Heidenheim (DE)

(72) Inventors: Axel Eckstein, Heidenheim (DE); Pierre Croizat, Herbrechtingen (DE); Cornelia Wolf, Herbrechtingen (DE)

(73) Assignee: PAUL HARTMANN AG, Heidenheim (DE)

( * ) Notice: Subject to any disclaimer, the term of this patent is extended or adjusted under 35 U.S.C. 154(b) by 704 days.

(21) Appl. No.: 13/962,765

(22) Filed: Aug. 8, 2013

(65) Prior Publication Data

US 2014/0046278 A1    Feb. 13, 2014

Related U.S. Application Data

(60) Provisional application No. 61/681,354, filed on Aug. 9, 2012.

(30) Foreign Application Priority Data

Aug. 9, 2012    (DE) .................. 10 2012 214 182

(51) Int. Cl.
*A61M 1/00*    (2006.01)
*A61M 35/00*   (2006.01)
*A61M 27/00*   (2006.01)

(52) U.S. Cl.
CPC .......... *A61M 35/00* (2013.01); *A61M 1/0084* (2013.01); *A61M 1/0088* (2013.01); *A61M 27/00* (2013.01)

(58) Field of Classification Search
CPC .............. A61M 1/0088; A61M 1/0084; A61M 1/0058; A61M 27/00; A61M 35/00
See application file for complete search history.

(56) References Cited

U.S. PATENT DOCUMENTS 8,795,247 B2 *  8/2014  Bennett ............. A61F 13/00068
                                                          604/319
2001/0031943 A1 * 10/2001 Urie .................... A61M 1/0088
                                                          604/43
(Continued)

FOREIGN PATENT DOCUMENTS

DE         33 27 586      2/1984
DE       102010006272     7/2011
(Continued)

*Primary Examiner* — Philip R Wiest
*Assistant Examiner* — Ariana Zimbouski
(74) *Attorney, Agent, or Firm* — Henry M. Feiereisen LLC.

(57) ABSTRACT

A connection device for use in the negative pressure therapy of wounds, includes a flexible conduit having at least two lumens and being constructed for impingement with negative pressure and/or fluid media; a coupling body made of an elastomeric flexible material, and non-detachably molded onto a wound-side end section of the conduit and being constructed for arrangement on a negative pressure bandage which covers the wound and seals the wound against the atmosphere, wherein the conduit communicates with a wound space through at least one opening in the coupling body; and a fluid inlet section for insertion through an opening in the negative pressure bandage into the wound space. The fluid inlet section is formed on the coupling body and protrudes over a walling of the coupling body, which walling faces the negative pressure bandage. The fluid inlet section is fluidly connected interiorly of the coupling body with a further lumen for delivering a fluid medium. The further lumen is formed inside the conduit or by a fluid delivery line leading to the coupling body.

21 Claims, 2 Drawing Sheets

(56) References Cited

U.S. PATENT DOCUMENTS

| | | | |
|---|---|---|---|
| 2005/0137539 A1* | 6/2005 | Biggie | A61M 1/0096 |
| | | | 604/313 |
| 2006/0100586 A1 | 5/2006 | Karpowicz et al. | |
| 2010/0063464 A1 | 3/2010 | Meyer et al. | |
| 2011/0152800 A1 | 6/2011 | Eckstein et al. | |
| 2011/0178481 A1* | 7/2011 | Locke | A61M 1/0088 |
| | | | 604/319 |
| 2011/0184362 A1 | 7/2011 | Croizat et al. | |
| 2012/0143156 A1 | 6/2012 | Bannister et al. | |

FOREIGN PATENT DOCUMENTS

| | | |
|---|---|---|
| EP | 1 129 734 A2 | 9/2001 |
| WO | WO 2011/087871 | 7/2011 |
| WO | WO 2011/113978 | 9/2011 |

* cited by examiner

CONNECTION DEVICE FOR USE IN THE NEGATIVE PRESSURE TREATMENT OF WOUNDS

CROSS-REFERENCES TO RELATED APPLICATIONS

This application claims the benefit of prior filed U.S. provisional Application No. 61/681,354, filed Aug. 9, 2012, and of German Patent Application, Serial No. 10 2012 214 182.0, filed Aug. 9, 2012, pursuant to 35 U.S.C. 119(e), the disclosure of which is incorporated herein by reference.

BACKGROUND OF THE INVENTION

The invention relates to a connection device for use in the negative pressure therapy of wounds The following discussion of related art is provided to assist the reader in understanding the advantages of the invention, and is not to be construed as an admission that this related art is prior art to this invention.

In the recent past, the negative pressure treatment of wounds, in particular of problematically healing wounds has gained increasing importance. Negative pressure treatment means that a body or wound area which is exposed to the surrounding atmosphere is sealed pressure tight or negative pressure tight against the environment i.e., the atmosphere in which we live and breathe, in a manner that will be described later, wherein a pressure which is lower relative to the atmospheric pressure, i.e., negative pressure can be applied and permanently maintained within the sealed wound region in a manner which is also to be explained below. Negative pressure in the context of the field at issue here, relates to a negative pressure of typically between 0 and 250 mmHg (mm mercury column) below the surrounding atmospheric pressure. This has been shown to facilitate wound healing. For the negative pressure tight sealing, a negative pressure bandage is provided, which for example can include a pressure tight—or negative pressure tight film layer, which is typically adhesively attached to an uninjured body region that surrounds the wound to achieve a tight sealing. In order to apply and maintain a negative pressure to the wound space based on a negative pressure generating device, i.e., a vacuum pump in the broadest sense, conduit to which negative pressure can be applied can be used in the systems for negative pressure therapy at issue here, which conduit interact with the negative pressure bandage in order to apply negative pressure to or into the wound space.

From unpublished DE 10 2011 082 341.7 a connection device of the generic type is known in which, for carrying out a so-called instill therapy, a fluid delivery line extends through the coupling body and protrudes into the wound space so that media that contain active agents can be delivered into the wound space. The passage of the fluid delivery line through the coupling body is associated with cost intensive manufacturing measures.

It would therefore be desirable and advantageous to provide an improved connection device so that when applying a negative pressure therapy to wounds, the connection device can at the same time be used for delivering media into the wound space, in particular media that contain active agents, be manufactured in a simple and economical manner and is reliable during use.

SUMMARY OF THE INVENTION

According to one aspect of the present invention, a connection device for use in the negative pressure therapy of wounds, includes: a flexible conduit having at least two lumens and being constructed for impingement with negative pressure and/or fluid media; a coupling body made of an elastomeric flexible material, wherein the coupling body is non-detachably molded onto a wound-side end section of the conduit and is constructed for arrangement on a negative pressure bandage which covers the wound and seals the wound against the atmosphere, wherein the conduit communicates with a wound space through at least one opening in the coupling body; and a fluid inlet section for insertion through an opening in the negative pressure bandage into the wound space, wherein the fluid inlet section is formed on the coupling body and protrudes over a walling of the coupling body, which walling faces the negative pressure bandage, wherein the fluid inlet section is fluidly connected interiorly of the coupling body with a further lumen for delivering a fluid medium, which further lumen is either formed inside the conduit or by an additional fluid delivery line which is led to the coupling body Via the lumen for delivering a fluid medium, fluids that facilitate wound healing and/or active agents contained in the fluid medium are can be delivered to the wound space (Instill therapy). Via at least one further lumen of the conduit, which at least one further lumen is configured as suction lumen, the fluid medium and as the case may be wound liquid is suctioned out of the wound space and conducted in the direction toward the negative pressure generating device and into a liquid collection container.

Preferably, the conduit of the connection device according to the invention is constructed flat and is initially manufactured separately, which has the general advantage of allowing an endless manufacturing, preferably by extrusion, wherein subsequent thereto sections of a respective desired line length can be generated by cutting. The coupling body is then formed by injection molding to an end section of the conduit and is finished by attaching and fastening of the end cap. Manufacturing the coupling body in this way has the particular advantage that a sealing transition to the conduit can be formed reliably or in other words, that when forming the coupling body the associated and provided conduit is sealingly attached to the coupling body.

The at least one opening in the walling of the coupling body, which walling faces the negative pressure bandage, can either be manufactured during the injection molding process by suitable configuration of the injection molding tool or in a subsequent work step for example by a punching process. However, manufacturing by injection molding is preferred. Preferably, multiple openings are provided, which are preferably configured as oblong holes.

It is further advantageous when the conduit leads to the coupling body essentially parallel to the plane of the two-dimensional extent of the coupling body. In this context, "essentially parallel" means a slant of up to 15° in relation to this plane of extent, which also forms the contact surface to the negative pressure bandage.

The fluid inlet section that protrudes from the coupling body can be configured in different manners. For example, it can be advantageous when the fluid inlet section is formed by the fluid delivery line that is led to the coupling body, and which extends through the coupling body, wherein the elastomeric, flexible material that forms the coupling body, can also be molded to the fluid delivery line. In this case, the fluid delivery line can thus be inserted into an injection molding tool together with the conduit and like the conduit can be integrated into the coupling body by injection molding-on elastomeric material. Also in the case when no additional fluid delivery line is provided but the conduit at the same time also forms the lumen for delivering the fluid medium, it is conceivable that the conduit extends through the coupling body with a section that delimits this lumen, and projects from the wound facing side of the coupling body.

According to another advantageous feature of the present invention, further variant of the present invention, the fluid inlet section can be configured one-piece with the coupling body in the injection molding process. In this variant, it is advantageous that the fluid delivery line or the conduit does not have to be bent to deviate from its essentially parallel extent in which it is led to the body surface.

According to another advantageous feature of the present invention the fluid inlet section can be configured as a conducting component which is manufactured separate from the coupling body and which is preferably sealingly inserted into and fixed in an opening in the walling of the coupling body which walling faces the negative pressure bandage, and is fluidly connected with the inside of the coupling body. This variant is advantageous because the complexity of the injection molding tool can be reduced. Only an opening which is in fluid communication with the inside of the coupling body has to be formed into which the fluid the fluid inlet section can then be inserted. The fluid inlet section may be fixed only by clamping or by using an adhesive.

According to another advantageous feature of the present invention the coupling body can be further configured by joining and preferably non-detachably fixing an end cap to the molded-on material, thereby sealing the coupling body tight against the outside. This has the advantage that the configuration of the injection molding tool is less complex and hollow spaces inside the coupling body which communicate with the lumens of the conduit, and are also referred to as lumens can be manufactured more easily. After the injection molding process, the coupling body can end open to the outside and is then closed by the end cap and completed. The end cap is preferably sealingly fixed with adhesive.

According to another advantageous feature of the present invention, the additional fluid delivery line, which leads to the coupling body, can be fluidly connected with the interior of the coupling body through this end cap. The end cap forms the part of the connection device via which or by means of which a fluid is delivered to the connection device for carrying out an instill therapy. This has the advantage that differently configured end caps can be manufactured and provided so that based on a manufactured unit composed of conduit with molded-on coupling body, connection devices can be produced which are suited for carrying out an instill therapy and those which are not suited for carrying out an instill therapy depending on which type of end cap is used for finishing the coupling body.

According to another advantageous feature of the present invention the end cap can have a connection device for the additional fluid delivery line that is led to the coupling body. The fluid delivery line is thus capable of being fluidly connected with the end cap in any appropriate manner, in the simplest case by a plug-in connection as interference fit. In this case the end cap itself has a through opening into the interior of the coupling body. It is possible that the fluid delivery line ends inside the end cap or extends through the end cap and protrudes into the interior of the coupling body or further protrudes over the wound facing side of the coupling body for simultaneously forming the fluid inlet section.

In the interior of the coupling body, preferably at least two lumens are formed which are each independently delimited and fluidly connected to lumens of the conduit.

According to another advantageous feature of the present invention, the coupling body can be configured so that at least one lumen ends freely after the injection molding-on, and so that by fastening the end cap, the freely ending lumen is sealed tight toward the outside.

According to another advantageous feature of the present invention, the coupling body can be configured so that after the injection molding-on, at least two lumens end freely and by fastening the end cap, the freely ending lumens are sealed tight toward the outside and are connected with one another so as to be in flow communication with each other, in that the end cap has a recess that connects the lumens with one another. This has the advantage that the lumens of the conduit or the coupling body are connected at their distal ends and thus without dead space.

This is particularly advantageous when one of the lumens is intended to function as rinsing lumen because in this case a complete rinsing of the lumens can be ensured without deposits forming at dead spaces that cannot, or only with difficulty, be circulated. The formation of this communication at the distal ends of the lumens by fastening and sealing of the end cap offers a very economical way of manufacturing the coupling body or the connection device. The end cap itself can be produced in an injection molding process as injection molded part.

According to another advantageous feature of the present invention, the conduit and the coupling body and preferably also the end cap can be made of a flexible elastomeric material, in particular of silicone or on silicone basis, which has a shore A—hardness of at most 65, in particular of at most 60, in particular of at most 50, in particular of at most 40, and further of at least 10 in particular of at least 15.

The end cap is preferably materially connected with the injection molded material of the coupling body, in particular and preferably bonded. Preferably, the end cap closes the coupling body in a rounded manner. A transition to the end cap is preferably essentially free of grooves and steps.

For perfecting the joining of the end cap, in a further embodiment of the invention, the coupling body can have a preferably thin border region in which the end cap is inserted and which surrounds the end cap collar-like. Such a border region which for example has a wall thickness of 0.2 to 1.5 mm can be very easily produced by the injection molding process because it only has to protrude by a few millimeters, for example 1 to 10 mm, in particular 1 to 8 mm, in particular 1 to 5 mm, in order to form a collar-like receptacle for the end cap.

According to another advantageous feature of the present invention, the coupling body can be configured with a first region which includes a part that at least partially surrounds the end section of the conduit, an adjoining intermediate part and the end cap, and with a second region which relative to the first region has a smaller thickness and extends two dimensionally. The mentioned intermediate part of the coupling body results when the end section of the conduit does not essentially extend over the entire longitudinal extent of the first region, but only forms a relatively short edge for injection molding-on the coupling body. In this case the lumens of the conduit continue in the interior of the coupling body by channel forming recesses i.e., by lumens which are formed during the injection molding. A configuration of the coupling body with a relatively short portion, which surrounds the end section of the conduit and an adjoining intermediate part in which the lumens of the conduit are continued, is preferred. In this case it is advantageous when the end section of the conduit, i.e., the region of the conduit that is surrounded with material of the coupling body, extends into the coupling body by about 2 to 15 mm and further in particular 3 to 12 mm and further in particular 5 to 10 mm.

According to another advantageous feature of the present invention the aforementioned two-dimensionally extending second region of the coupling body can be configured to have a thickness of 0.1 to 2 mm, in particular 0.1 to 1.5 mm, in particular 0.1-11.0 mm, in particular 0.1-0.8 mm, in particular 0.1-0.5 mm.

Advantageously, the second region has a two-dimensional extent so that a contact surface of the second region with the wound averted top side of the negative pressure bandage is at least 1.5 times, in particular at least 1.8 times as the size of the contact surface of the first region. The contact surface is calculated or viewed in the perpendicular projection onto the plane of extent of the coupling body.

According to another advantageous feature of the present invention, it the first region of the coupling body can extend the longitudinal extent of the conduit and the second region of the coupling body flanks the first region on both sides of its longitudinal extent and when viewed from the top has a butterfly-like shape, i.e., it has a constriction on both sides of the longitudinal extent.

According to another advantageous feature of the present invention, the maximal thickness of the first region of the coupling body which is molded to the conduit is at most 3 mm, in particular at most 2 mm greater than the thickness of the conduit, and that the width of the first region of the coupling body is at most 5 mm, in particular at most 3 mm, in particular at most 2 mm greater than the width of the conduit.

According to another advantageous feature of the present invention, the extent of the thickness of the conduit is at most 7 mm, in particular at most 6 mm, in particular at least 3 mm and further 4-6 mm, wherein its width transverse to the longitudinal extent is at least 12 mm, in particular at least 15 mm, in particular between 15 mm and 30 mm, in particular between 15 mm and 25 mm, in particular between 15 mm and 22 mm.

According to another advantageous feature of the present invention, a first lumen of the conduit forms a rinsing lumen, i.e., a lumen for delivering fluid media, in particular air, to the coupling body and that a second lumen of the conduit forms a suction lumen to which negative pressure is applied for draining fluid media from the wound in the direction toward a negative pressure generating device, and when the second lumen has a greater cross section than the first lumen. The suction lumen which is formed with a greater conducting cross section can in this case be used for disposal of wound secrete which often times contains particle shaped components.

It is particularly advantageous when the coupling body includes at least three lumens that extend adjacent one another, wherein a first lumen is configured as rinsing lumen, wherein at least a second lumen is configured as suction lumen, and wherein a third lumen forms the lumen for delivering a fluid medium to the wound, i.e., into the wound space, and when the rinsing lumen and the suction lumen are fluidly connected to each other at their ends. It can further be advantageous when the lumen that is configured as suction lumen is closed in the direction toward the wound, i.e., it is formed without an opening and in this case is fluidly connected with the further lumens inside the coupling body only via its distal end. As explained before, this can be advantageously realized by a flow communication via the end cap.

For joining the connection device to the negative pressure bandage, it is advantageous that a side of the coupling body, which faces toward the negative pressure bandage, is formed with an adhesive layer or an adhesive coating, in order to generate a bonding connection with the negative pressure bandage which is essentially negative pressure tight against the environment, thus enabling the intended use of the connection device.

According to another advantageous feature of the present invention, the adhesive layer or coating can be formed by an at least three-layered adhesion-providing layer, which includes a center carrier layer, a first adhesive layer which is held on the carrier layer and faces the coupling body and a second adhesive layer which is held on the carrier layer and faces away from the coupling body. The adhesion-providing layer is configured so as to not block the at least one opening in the coupling body and so that the first adhesive layer and the second adhesive layer are formed by different adhesive materials with different adhesive properties. In the case when the coupling body is formed from silicone, it is advantageous that the first adhesive layer includes a silicone glue. It is further advantageous when the second adhesive layer includes an acrylate glue which is generally suited to enter into an essentially negative pressure tight connection with typical wound bandage materials. Preferably, the first and second adhesive layers have a thickness of 20 to 400 µm. In the center carrier layer, a nonwoven, a flat material with a textile bonding, such as for example a knitted or woven fabric, or a plastic foil, a metal foil or a composite material made thereof is preferred. It is further advantageous when the wound facing side of the second adhesive layer is covered by a detachable protective layer, which is preferably configured two-part and is further preferably provided with a finger tab and/or a gripping region that protrudes over the second adhesive layer.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Throughout all the Figures, same or corresponding elements are generally indicated by same reference numerals.

These depicted embodiments are to be understood as illustrative of the invention and not as limiting in any way. It should also be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

The Figures show a connection device according to the invention generally designated with the reference numeral 2 for use during the negative pressure therapy of wounds. For this, the connection device 2 is connectable with a here not shown negative pressure generating device, which typically interacts with a liquid receiving container for separating and collecting wound secrete and rinsing medium that is suctioned from the wound space. The connection device serves for negative pressure tight coupling to a negative pressure bandage 12, which again seals essentially negative pressure tight against the environment, wherein a negative pressure communication to the wound space is generated.

The connection device 2 according to the invention includes a conduit overall designated with the reference numeral 4 and a coupling body 6. The coupling body 6 is, in a manner to be described in more detail below, molded to a wound side end section 8 of the conduit 4 in a plastic-injection molding process.

A wound-averted end of the conduit 4 is connectable with a not shown negative pressure-generating device.

The coupling body 6 includes a first region 16, which in the exemplary shown case is block-shaped and extends the longitudinal extent of the conduit 4, and a second region 18 which compared to the first region has a significantly smaller thickness and extends two dimensionally and starting from the first region 16 preferably extends two dimensionally away on both sides of the first region and further preferably on at least three sides of the first region 16, thereby allowing to realize a great connection surface between the coupling body 6 and the negative pressure bandage 12.

The first region 16 of the coupling body 6 includes a part 20 which at least partially surrounds the end section 8 of the conduit 4, an intermediate part 24 adjoining the part 20 in a longitudinal direction 22, and an end cap 26. The part 20 which surrounds the end section, the intermediate part 24 and the two dimensionally extending second region 18 of the coupling body 6 are produced one-piece from a flexible elastomeric material, preferably from silicone or on silicone basis. For this, the conduit 4 or the wound side end section 8 of the conduit 4 is introduced into a not shown injection mold, and the elastomeric material that forms the coupling body 6 is molded onto the end section 8 of the conduit 4. The injection mold is configured or equipped, so that lumens 28, 30, 31 of the conduit 4 that form flow channels are continued inside the coupling body 6. Corresponding means that form hollow spaces or channels have thus to be provided in the injection molding tool, in particular in the form of rods or the like. Even though not shown, it would also be conceivable that the conduit 4 or its end section 8 extends up to the end cap 26. In this case the part 20 which at least partially surrounds the end section 8 of the conduit 4, would be configured longer in longitudinal direction 22 and the intermediate part 24 would not be required or be configured much shorter. However, it has proven advantageous when the conduit 4 only protrudes into the coupling body 6 with a relatively short end section 8, because in this case the freedom of design of the coupling body 6 inside the intermediate part 25 is greater and openings 32 in a walling 34 of the coupling body 6 which walling 34 faces the negative pressure bandage can already be formed in the injection molding process.

The intermediate part 24 is thus formed with lumens 36, 38, 40 in its interior that are separated from one another transverse to the longitudinal direction 22 and adjoin the lumens 28, 30, 31 of the conduit 4 as can be seen from the Figures.

Figure 1:
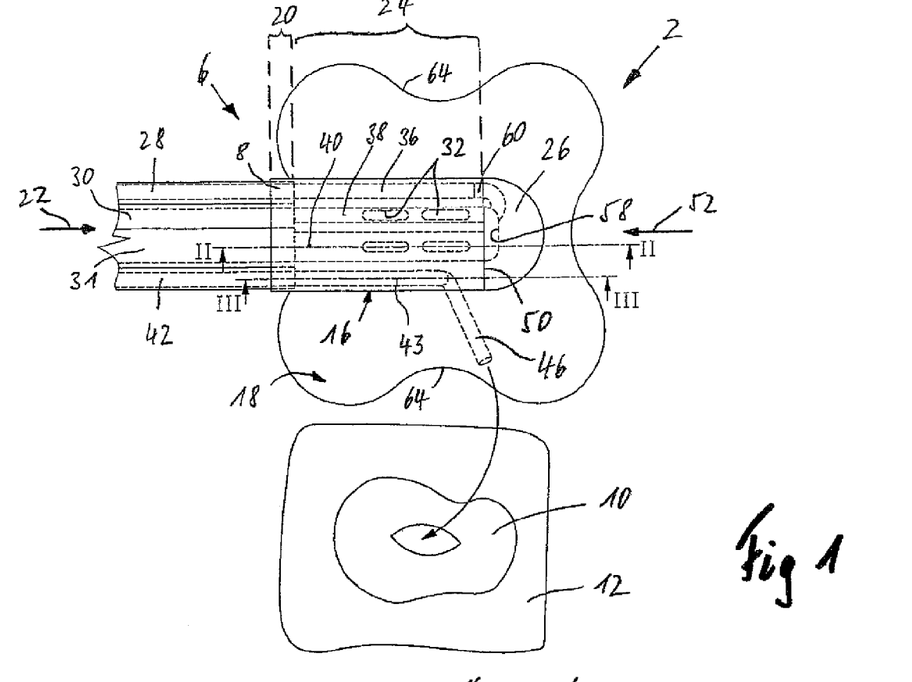
FIG. 1 shows a top view onto a connection device according to the invention for use during the negative pressure treatment of wounds, and an outlined wound with a negative pressure bandage.
Figure 3:
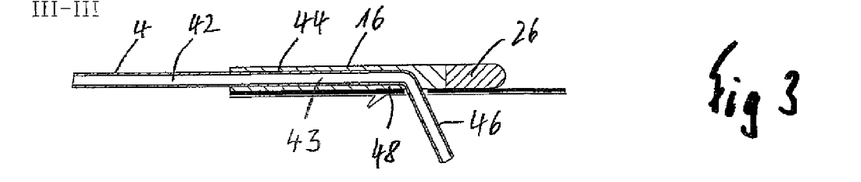
FIG. 3 shows a sectional view of the connection device according to FIG. 1 with sectional plane III-III.

It can further be seen from FIG. 1 that a further lumen 42 is formed in the conduit 4, which lumen 42 serves for delivering a fluid medium to the wound space, which medium in particular contains active agents. As can be seen from FIG. 3, the conduit 4 extends through the coupling body 6 with a line section 44, which forms and delimits the lumen 42. This line section 44 is thus also surrounded with elastomeric material by injection molding and delimits lumen 43. In the exemplary shown case, this line section 44 curves in the direction toward the wound space and forms a fluid inlet section 46 which protrudes over a walling of the coupling body 6, which walling faces the negative pressure bandage 10.

Figure 2:
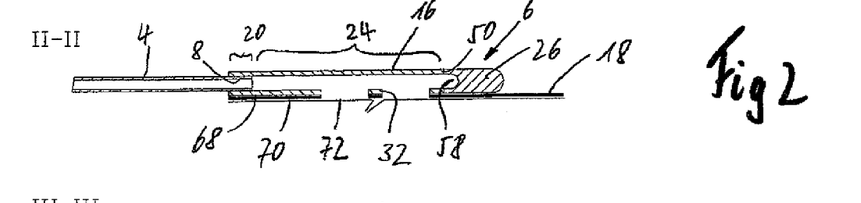
FIG. 2 shows a schematic sectional view of the connection device according to FIG. 1 with the sectional plane II-II.
Figure 4:
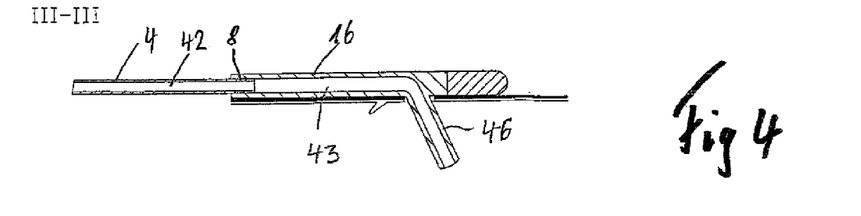
FIG. 4 shows a sectional view of a further embodiment of the connection device with corresponding sectional plane III-III.

FIG. 4 shows a further embodiment, in which the conduit 4 ends over its entire width in a manner as shown in FIG. 2, so that the aforementioned line section 44 is not provided but instead the lumen 42 is continued by and delimited by a corresponding hollow space forming lumen 43 inside the coupling body 6 for delivering a fluid medium. In this case, the fluid inlet section 46 can either be produced one-piece with the elastomeric material of the coupling body 6 in the injection molding process as shown in FIG. 4, or it is formed by an additional conducting piece which is inserted into a correspondingly configured opening in the walling 48 of the coupling body.

It can be seen particularly from FIGS. 1 and 2 that the lumens 36, 38, 40 of the coupling body 6 end freely on a front side 50 of the intermediate part 24, which front side 50 faces the end cap 26. They are sealed against the environment by attachment and negative-pressure tight fastening of the end cap 26. The end cap 26, which is fastened by interference fit or preferably non-detachably by material connection, in particular by means of glue, completes the coupling body 6 of the connection device 2 according to the invention. When injection molding-on the elastomeric material that forms the coupling body 6, a not shown border region, which extends in opposite direction to a direction 52 in which the end cap 26 is attached can be formed, which border region delimits a receiving opening for the end cap 26. This border region then surrounds the end cap 26 collar-like. Preferably, the border region is relatively thin-walled for example only 0.5 to 1.5 mm thick. The border region extends preferably over three sides, so that the receiving opening is delimited on the fourth side by the two dimensionally extending second region 18 of the coupling body.

The end cap 26 is configured so as to adjoin the intermediate part 24 of the coupling body 6 essentially without grooves or steps.

The end cap 26 is further configured with a recess, overall designated with the reference numeral 58, by means of which recess 58 a flow communication between at least two lumens, in the exemplary shown case between all three lumens 36, 38, 40 is achieved, i.e., starting from their distally ending openings in the region of the front side 50. The recess 58 can be realized in different ways, in the simplest case for example in the form of an oblong hole, which then adjoins the front side of the intermediate part 24. The end cap 26 is formed with a tubular attachment 60 which when attaching the end cap 26 sealingly engages in the lumen 36 in the intermediate part 24, which lumen 36 is configured complementary to the attachment 60. In the interior of the end cap 26, this tubular attachment 60 leads into the transverse extending recess 58, which opens in the shape of an oblong hole toward the front side 50 of the intermediate part 24. In this way, a flow communication exists between the lumens 36, 38, 40. In the exemplary shown case, the lumen 28 of the conduit 4 and the lumen 36 inside the coupling body 6 adjoining the conduit 4 serve as rinsing lumens for delivering a fluid rinsing medium (air or rinsing liquid). In this way, fluid rinsing media are conducted to the distal end openings of the lumens 38, 40 in the front side 50 of the intermediate part 24, thereby allowing a dead space free rinsing; there is thus no line region which is not immediately affected by the flow along the path of the flow, which is particularly beneficial with regard to the intended functioning of the connection device, the negative pressure therapy carried out therewith and with regard to a reduction of bacterial growth and infections. The end cap 26 thus has a dual function, i.e., on the one hand, it completes the coupling body 6 and closes the openings of the lumens 36, 38, 40 which end open after the injection molding process, and on the other hand the end cap 26 results in a flow communication between the lumens 36, 38, 40.

For negative pressure communication between the wound space, the already mentioned openings 32 are formed in the walling 34 of the coupling body 6, which walling 34 faces the negative pressure bandage. It can be seen from the Figures that the lumen 36 of the coupling body, which functions as rinsing lumen is not provided with such an opening, which is preferred, however not strictly required. The openings 32 which are provided in the region of the longitudinal extent of the lumens 38, 40 are preferably formed as oblong holes and have an preferred length of for example 8 to 12 mm. In the exemplary shown case, two of such oblong hole shaped openings are formed along the extent of each lumen 38, 40. During use, the lumens 38, 40 of the coupling body communicate via these openings 32 and via at least one opening in the negative pressure bandage with the wound space. Typically, negative pressure is applied to the lumens 38, 40 of the coupling body 6 via the lumens 30, 31 in the conduit 4; the lumens 38, 40 thus typically function as suction lumens for applying negative pressure and for discharging wound secrete, rinsing liquid or other supplied fluid media.

Figure 5:
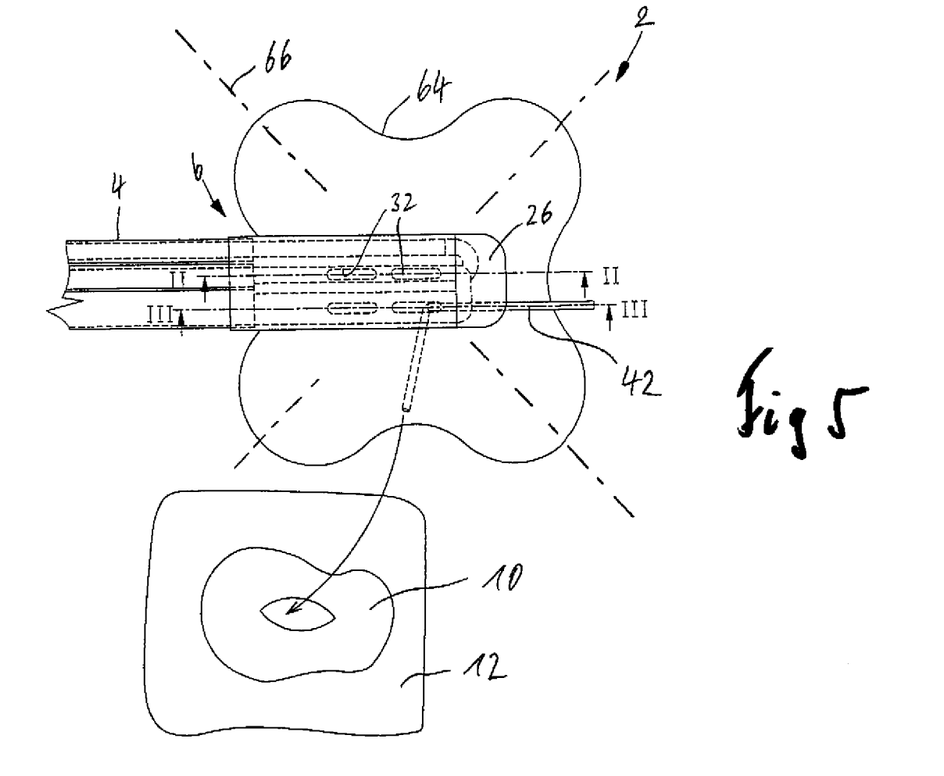
FIG. 5 shows a top view onto a further embodiment of the connection device according to the invention with outlined wound and negative pressure bandage.
Figure 6:
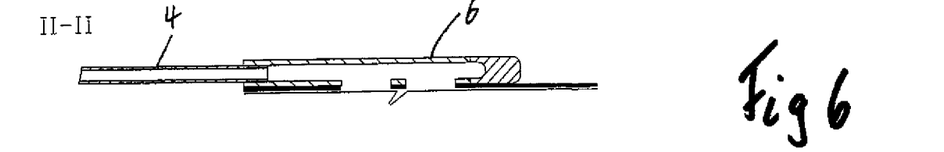
FIG. 6 shows a sectional view of the connection device according to FIG. 5 with sectional plane II-II.
Figure 7:
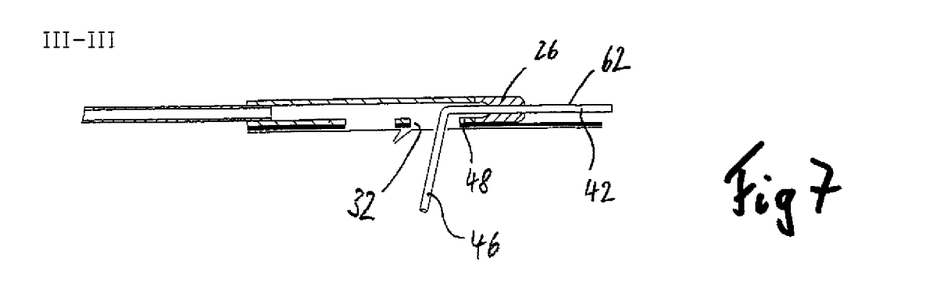
FIG. 7 shows a sectional view of the connection device according to FIG. 5 with sectional plane III-III.

FIGS. 5 to 7 show a further embodiment of the connection device according to the invention in which the lumen 42 for delivering a fluid medium to the wound space is not formed by the conduit 4 but by an additional fluid delivery line 62 which however is also led to the coupling body 6 approximately parallel to the two dimensional extent of the connection device 2. The fluid delivery line 62 can for example be led to the coupling body 6 adjacent and parallel to the conduit 4 (not shown). In the exemplary shown case, the fluid delivery line 62 extends through the end cap 26 into the interior of the coupling body 6 and from there through an opening 32 in the walling 48 of the coupling body 6, which walling faces the bandage, into the wound space. The end of the fluid delivery line 62 thus forms a fluid inlet section 46, which protrudes from the side of the coupling body 6, which side faces the wound and can protrude into the wound space of the wound 10 through a further opening in the wound bandage. It is conceivable that the fluid delivery line 62 is only inserted into a through opening of the end cap 26 and that the fluid inlet section 46 is then either configured one-piece with the coupling body 6 or is formed by a line section which is inserted into an opening of the coupling body 6.

In the embodiment according to the FIGS. 5-7, the conduit 4 is preferably only configured with three lumens.

In the following, the shape of the two dimensionally extending second region 18 of the coupling body 6 which is exemplary shown in the Figures, is described. This shape or form can be most accurately described as butterfly-shape, because this second region 18 when viewed in longitudinal direction 22 has a constriction 64 on both sides. In this way, the dimensions of the coupling body 6 or its second region 18 are greater along outlined diagonals 66, which form an angle of about 45° with the longitudinal axis, than in the longitudinal direction and perpendicular thereto. In the exemplary and preferred shown case, the two dimensionally extending thin second region 18 extends toward three sides past the also rather flat, however block-shaped first region 16 of the coupling body 6. In this way, a very good connection to a not shown negative pressure wound bandage can be achieved, because the occurring forces are distributed evenly across a great surface and therefore are conducted into the regions of the wound bandage that surround the wound and the body surface of the patient without local peak forces.

For connection to the negative pressure bandage, the coupling body includes on its side 68 that faces the negative pressure bandage an adhesive layer 70 and a detachable cover layer 72. The adhesive layer 70 is preferably configured as an at least three-layered adhesive-providing layer which includes a center carrier layer, a first adhesive layer that is held on the carrier layer and faces the coupling body and a second adhesive layer that is held by the carrier layer and faces away from the coupling body. The adhesive layers are each optimized with regard to the formation of an adhesive connection with the material of the coupling body or with the material of the negative pressure bandage. With regard to further features of this at least three-layered adhesive providing layer reference is made of the non-published DE 10 2011 108 726.9, the content of which is herewith incorporated by reference into the present application.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

1. A connection device for use in the negative pressure therapy of wounds, comprising:
   a flexible conduit having at least two lumens and being constructed for impingement with negative pressure and/or fluid media;
   a coupling body made of an elastomeric flexible material, said coupling body being non-detachably molded onto a wound-side end section of the conduit and being constructed for arrangement on a negative pressure bandage which covers the wound and seals the wound against the atmosphere, said conduit communicating with a wound space through at least one opening in the coupling body;

a fluid inlet section for insertion through an opening in the negative pressure bandage into the wound space, said fluid inlet section being formed on the coupling body and protruding over a walling of the coupling body, which walling faces the negative pressure bandage, said fluid inlet section being fluidly connected interiorly of the coupling body with a further lumen for delivering a fluid medium, wherein the coupling body comprises at least three other lumens extending adjacent one another, wherein a first one of the at least three other lumens is configured as rinsing lumen, wherein at least one second one of the at least three other lumens is configured as suction lumen, wherein a third one of the at least three other lumens is constructed for delivering a fluid medium to the wound, and wherein the rinsing lumen and the suction lumen are fluidly connected at their ends, and wherein the rinsing lumen is closed in a direction of the wound and is fluidly connected with one or more other ones of the at least three lumens only via its distal end; and an end cap attached to the coupling body, thereby sealing the coupling body tight against the environment.

2. The connection device of claim 1, wherein the further lumen is formed inside the conduit.

3. The connection device of claim 1, wherein the fluid inlet section is produced separate from the coupling body, and received in an opening in a walling of the coupling body, said walling facing the negative pressure bandage, said opening being fluidly connected with the interior of the coupling body.

4. The connection device of claim 3, wherein the fluid inlet section is sealingly received in the opening in the walling of the coupling body.

5. The connection device of claim 1, wherein the end cap is non-detachably fastened to the molded-on material of the coupling body.

6. The connection device of claim 1, wherein at least two other lumens are formed in the interior of the coupling body, said at least two other lumens being delimited independent from each other and fluidly connected with the at least two lumens of the conduit.

7. The connection device of claim 6, further comprising an end cap fastened to the coupling body, wherein at least one of the at least two other lumens of the coupling body ends freely, and is closed by the fastened end cap so as to be sealed to the outside.

8. The connection device of claim 7, wherein at least two of the at least two other lumens of the molded-on coupling body end freely, and are closed by the fastened end cap so as to be sealed to the outside and so as to be in flow communication with each through a recess of the end cap.

9. The connection device of claim 1, wherein the conduit and the coupling body are made of an elastomeric flexible material, having a shore A—hardness of at most 65 and at least 10.

10. The connection device of claim 1, wherein the end cap is connected to, the coupling body by material bonding.

11. The connection device of claim 1, wherein the coupling body has a border region, in which the end cap is inserted and which surrounds the end cap collar-like.

12. The connection device of claim 1, wherein the coupling body has a first region and a second region, said first region comprising a first part which at least partially surrounds the end section of the conduit, an intermediate second part adjoining the first part, and the end cap, said second region being defined by a smaller thickness than a thickness of the first region and extending two-dimensionally.

13. The connection device of claim 1, wherein the end section of the conduit extends into the coupling body about 2 to 20 mm.

14. The connection device of claim 12, wherein the thickness of the second region of the coupling body is 0.1-2.0 mm.

15. The connection device of claim 12, wherein the second region extends two-dimensionally so that a contact surface of the second region with a wound-averted top side of the negative pressure bandage is at least 1.5 times as large as a contact surface of the first region with the wound-averted top side of the negative pressure bandage.

16. The connection device of claim 12, wherein the first region of the coupling body extends along a longitudinal extent of the conduit and the second region of the coupling body flanks the first region on both sides of a longitudinal extent of the first region and when viewed from the top is shaped butterfly-like.

17. The connection device of claim 1, wherein a maximal thickness of the first region of the coupling body which is molded onto the conduit is at most 3 mm, greater than the thickness of the conduit and wherein the width of the first region of the coupling body is at most 5 mm greater than the width of the conduit.

18. The connection device of claim 1, wherein a thickness of the conduit is at most 7 mm, and at least 3 mm, and wherein a width of the conduit transverse to a longitudinal extent of the conduit is at least 12 mm.

19. The connection device of claim 1, wherein a first one of the at least two lumens of the conduit forms a rinsing lumen for delivering fluid rinsing media to the coupling body, and wherein a second one of the at least two lumens of the conduit forms a suction lumen for discharge of fluid media from the wound in a direction toward a negative pressure generating device, said suction lumen being constructed for impingement with negative pressure, said second lumen having a greater cross section than the first lumen.

20. The connection device of claim 1, wherein the rinsing lumen is fluidly connected with one or more other ones of the at least three lumens only via the end cap.

21. A connection device for use in the negative pressure therapy of wounds, comprising:

a flexible conduit having at least two lumens and being constructed for impingement with negative pressure and/or fluid media;

a coupling body made of an elastomeric flexible material, said coupling body being non-detachably molded onto a wound-side end section of the conduit and being constructed for arrangement on a negative pressure bandage which covers the wound and seals the wound against the atmosphere, said conduit communicating with a wound space through at least one opening in the coupling body; and a fluid inlet section for insertion through an opening in the negative pressure bandage into the wound space, said fluid inlet section being formed on the coupling body and protruding over a walling of the coupling body, which walling faces the negative pressure bandage, said fluid inlet section being fluidly connected interiorly of the coupling body with a further lumen for delivering a fluid medium, wherein a side of the coupling body which faces the negative pressure bandage is configured with an adhesive layer or an adhesive coating, for forming a negative pressure tight adhesive connection to the negative pressure bandage, and wherein the adhesive layer or coating is formed by an at least three-layered adhesion-providing layer, said adhesion-providing layer comprising a center carrier layer, a first adhesive layer which is held on the carrier layer and faces the coupling body and a second adhesive layer which is held on the carrier layer and faces away from the coupling body, wherein the adhesion-providing layer is configured so that the at least one opening in the coupling body is not blocked and so that the first adhesive layer and the second adhesive layer are formed from different adhesive materials and have different adhesive properties.

* * * * *